United States Patent [19]

Howe

[11] Patent Number: 4,815,972

[45] Date of Patent: Mar. 28, 1989

[54] DENTAL INTRUSION DEVICE

[76] Inventor: Raymond P. Howe, 13826 Rustic Dr., Gregory, Mich. 48137

[21] Appl. No.: 927,831

[22] Filed: Nov. 6, 1986

[51] Int. Cl.⁴ ............................................. A61C 3/00
[52] U.S. Cl. ........................................ 433/5; 433/17; 433/18
[58] Field of Search .................... 433/5, 6, 17, 18, 21, 433/24, 20

[56] References Cited

U.S. PATENT DOCUMENTS

| | | | |
|---|---|---|---|
| 3,401,457 | 9/1968 | Hickham | 433/5 |
| 3,494,034 | 2/1970 | Kesling | 433/17 |
| 3,638,313 | 2/1972 | Cervera | 433/5 |
| 3,798,773 | 3/1974 | Northcutt | 433/19 |
| 3,866,322 | 2/1975 | Broussard et al. | 433/5 |
| 4,087,915 | 5/1978 | Andrews | 433/5 |
| 4,212,637 | 7/1980 | Dougherty et al. | 433/5 |
| 4,330,272 | 5/1982 | Bergersen | 433/6 |
| 4,588,380 | 5/1986 | Toll | 433/5 |
| 4,650,182 | 3/1987 | Ross | 433/5 |

OTHER PUBLICATIONS

Opa, Inc., "The Opa: A Device for Vertical Control", 07 May 1979.
Northwest Orthodontics, Catalog and Technical Information, "Calibrated Extraoral Force, Controlled Intraoral Force", 6 Oct. 78.
Great Lakes Orthodontic Laboratories, Inc., "The Forward Movement", May 1979.

Primary Examiner—Robert Peshock
Assistant Examiner—Adriene J. Lepiane
Attorney, Agent, or Firm—Rhodes and Boller

[57] ABSTRACT

A dental intrusion device for intruding one or more teeth of a dental arch. Plural embodiments of the device are disclosed within the generic context of an intra-oral structure operatively related to the arch, an extra-oral structure, and a force-creating mechanism extending between the intra- and extra-oral structures. The co-action of these components results in intrusion forces being developed on teeth which are to be intruded. Various features within the generic aspect of the invention relate to particular forms of force-applying mechanism, particular forms of intra-oral structures and particular forms of extra-oral structures.

33 Claims, 7 Drawing Sheets

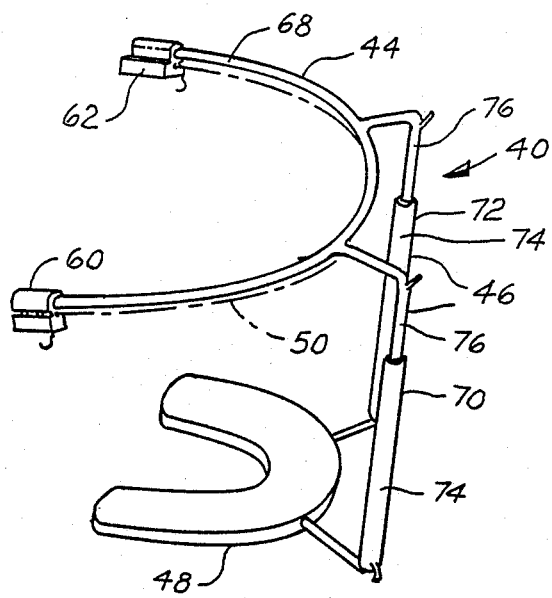
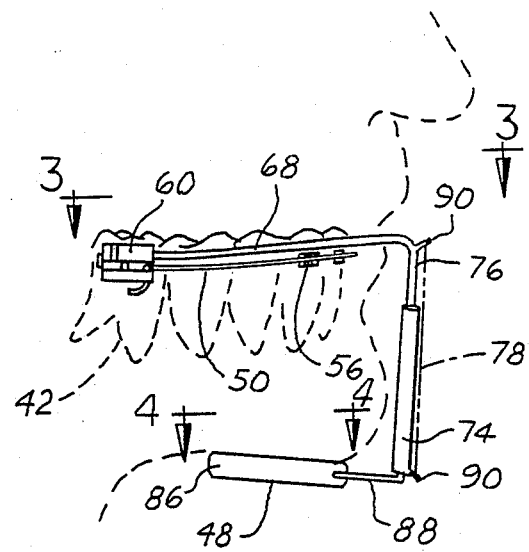
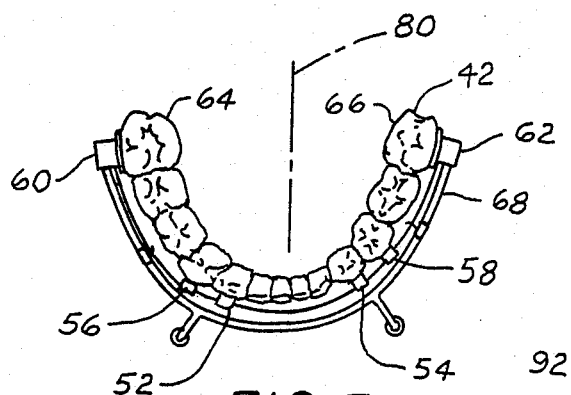
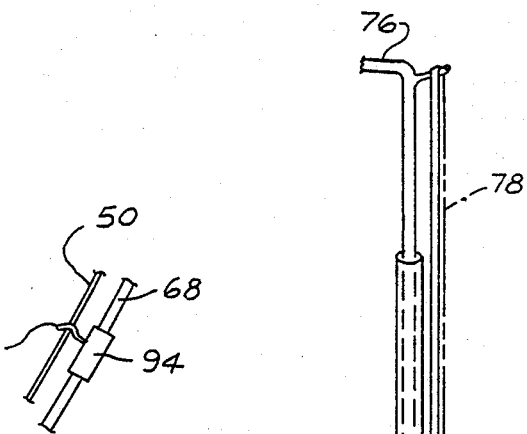
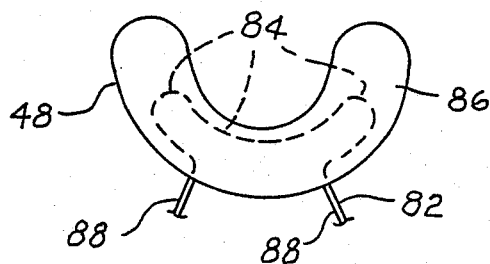
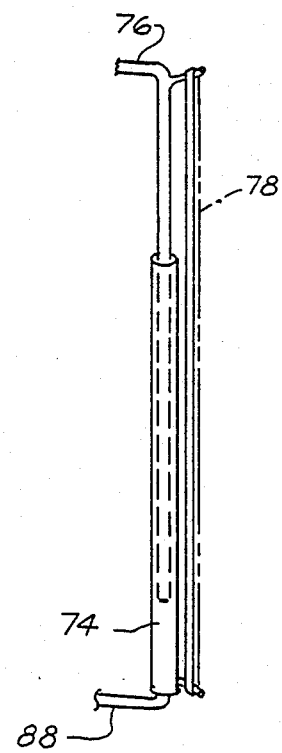
FIG. 1
FIG. 2
FIG. 3
FIG. 3A
FIG. 4
FIG. 5

1

DENTAL INTRUSION DEVICE

BACKGROUND AND SUMMARY OF THE INVENTION

This invention relates generally to orthodontic devices and more specifically it relates to novel devices for use in dental intrusion.

Certain orthodontic patients have dental conditions in which one or more teeth protrude from the gingiva in more than an optimum amount. This can adversely affect function, such as bite, as well as affecting appearance. Accordingly, orthodontic treatment procedures which are capable of intruding excessively protruding teeth will be highly beneficial in the treatment of such individuals.

While procedures for treatment of orthodontic conditions involves the use of particular appliances for particular conditions, many appliances are not solely intra-oral. Extra-oral components, such as headgear, chin cups, etc., are frequently used in association with intra-oral components in the treatment of certain conditions. It appears however, that an extra-oral component such as a chin-cup has not heretofore been used in association with an intra-oral component to perform tooth intrusion.

In its generic aspects, the present invention relates to dental intrusion devices having both extra- and intra-oral components coacting in a novel and unique manner to perform tooth intrusion. In the disclosed preferred embodiment, the intra-oral component comprises a means for mesio-distally spanning a selected portion of the lower arch and for acting on at least some of the teeth so spanned including one or more teeth to be intruded. An extra-oral component in the form of a chin cup, or chin pad, provides external stabilization of the appliance. These extra- and intra-oral components are rendered coactive by a force-creating means extending between them to cause intrusion forces to be developed on those teeth of the lower arch which are to be intruded.

The dental intrusion device of the present invention is relatively compact, readily adaptable to individual patients, and can be used in combination with other components, such as a Herbst mechanism for example, for the concurrent treatment of other conditions.

A number of different embodiments of the invention are disclosed. They possess singularly unique features which are useful not only in the disclosed appliances, but in other appliances as well. One such feature relates to the means of attachment of the arch-spanning wire to a buccal tube which is attached to a molar tooth. Another relates to an adaptaion to a buccal tube to increase the number of wires which can be connected to it. These features make the devices especially convenient for placement and removal and render them adaptable for use with patients who are already undergoing treatment.

Various embodiments of the force-creating means are disclosed, as well as various embodiments of the intra- and extra-oral components. These various embodiments possess certain individual characteristics which are useful in adapting the devices to the needs of particular individual patients.

The foregoing features, advantages and benefits of the invention, along with additional ones, will be seen in the ensuing description and claims which should be considered in conjunction with the accompanying drawings. The drawings disclose a presently preferred embodiment of the invention according to the best mode contemplated at the present time in carrying out the invention.

BRIEF DESCRIPTION OF THE DRAWINGS

FIG. 1 is a perspective view of a first embodiment of dental intrusion device embodying principles of the invention.

FIG. 2 is a side elevational view of the device of FIG. 1 illustrating the device in use.

FIG. 3 is a view taken in the general direction of arrows 3—3 in FIG. 2.

FIG. 3A is an enlarged view of a portion of FIG. 3 showing further detail.

FIG. 4 is a view taken in the general direction of arrows 4—4 in FIG. 2.

FIG. 5 is an enlarged view of a portion of the device looking in the same direction as the view of FIG. 2.

DESCRIPTION OF THE PREFERRED EMBODIMENT

Figure 6:
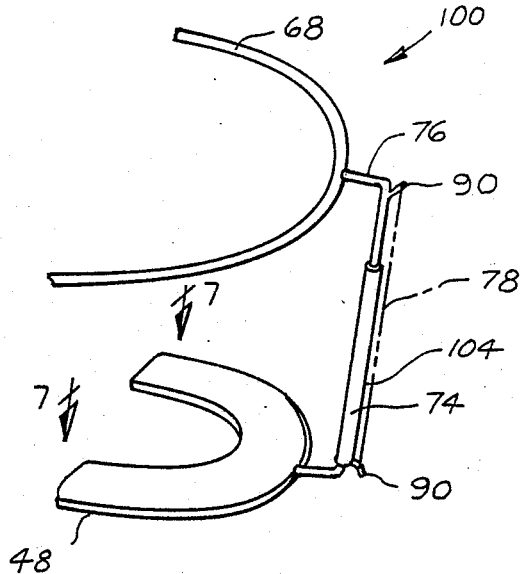
FIG. 6 is a perspective view similar to FIG. 1 illustrating a second embodiment of device.

FIGS. 1 through 5 portray a first embodiment of dental intrusion device 40 embodying principles of the present invention. FIG. 2 shows the device in patient use for intruding teeth of the patient's lower dental arch 42.

Generically, intrusion device 40 may be considered to comprise: an intra-oral means 44 for mesio-distally spanning a selected portion of arch 42 and for acting on certain of the teeth so spanned including those to be intruded; and a force-creating means 46 which extends from intra-oral means 44 to an extra-oral means 48. The two means 44, 48 react the forces developed by force-creating means 46. The means 48 serves to react force in a manner which stabilizes the appliance during the intrusion treatment procedure while the means 44 reacts force by transmitting force components to the teeth to be intruded such that intrusion forces are applied to those teeth.

In the illustrated embodiment of device 40 and the example of use shown in FIGS. 1 and 2, the means 48 comprises a chin pad, or rest, which bears against the underside of the chin. The teeth of arch 42 are spanned and joined by a conventional fine arch wire 50 secured to six brackets 52, 54, 56, 58, 60, and 62 which are attached to six individual teeth. In the illustrated embodiment, the distal ends of the arch wire are received in, and secured in conventional manner to, buccal tubes in the two brackets 60, 62 which are attached to the two molar teeth 64, 66 respectively. The device has a heavier arch-shaped wire 68 also received in the buccal tubes on brackets 60, 62 and is essentially co-extensive along the arch with the fine arch wire 50.

The force-creating means 46 comprises two pairs 70, 72 of telescoping members 74, 76 and rubber bands 78. Each pair and the associated rubber band is disposed to a corresponding side of a medial plane 80. The detailed construction comprises a wire 82 formed to have an intermediate portion 84 shaped as shown in FIG. 4. and embedded in the body 86 of the chin pad. The external end segments 88 of wire 82 project outwardly from the anterior face of the chin pad body and serve to support the force-creating means 46 in generally upright position.

The members 74, 76 are in the respective forms of circular cylindrical tubes 74 and rods 76. The lower ends of tubes 74 are secured to the end segments 88 of wire 82. Attachment of the tubes to the wire is accomplished in any suitable manner of fabrication such as by soldering. The open upper ends of the tubes receive the lower ends of the rods 76 with a telescopic sliding fit. The upper ends of the rods are bent inwardly and join to wire 68 in any suitable manner, such as soldering.

The telescoping members 74, 76 enable the two means 44, 48 to be bodily displaced toward and away from each other in a generally vertical sense. The force is actually developed by tensioning of the rubber bands 78 which are cooperatively associated with the telescopically engaged members in the manner portrayed in FIGS. 2 and 5. Small hooks 90 are provided on the two members 74, 76 of each pair. Each rubber band, which is of appropriate length and tension, is looped around the two hooks 90 serving to urge the corresponding members 74, 76 into increasing telescopic engagement and hence urge the chin pad and the wire 68 toward each other. Consequently, when the device is in use as in FIG. 2, a force is exerted by the device on the buccal tubes of brackets 60, 62, and this results in a downward intrusion force being applied to certain teeth of the lower arch.

It is to be understood that the illustrated example is intended to be merely representative, particularly with regard to the manner in which the teeth of the arch are mesio-distally spanned and operatively related. The force developed by the force-creating means 46 and the reaction thereof at the molar buccal tubes of brackets 60, 62 give rise to a clockwise torque, as viewed in FIG. 2; and it is transmitted along the fine arch wire to the brackets on individual teeth of the arch resulting in intrusion forces on those teeth. Over the course of a treatment procedure these teeth will be intruded into the gingiva.

As an aid in operatively relating wire 68 to the arch, additional means may be used. These are shown in FIGS. 3 and 3A to comprise small hooks 92 located mesially of the molar brackets 60, 62. The hooks extend from sleeves 94 which have a close fit on wire 68. The ends of the hooks are hooked onto the fine arch wire 50 in such a manner that a portion of the force which would otherwise be reacted at the buccal tubes on the molar brackets 60, 62 is reacted on the fine arch wire via the hooks. The sleeves 72 can be left slideable on the wire or alternatively can be crimped in place on the wire at a desired location along the wire's length.

Figure 7:
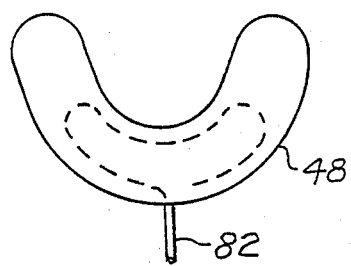
FIG. 7 is a view taken in the direction of arrows 7—7 in FIG. 6.

FIGS. 6 and 7 portray a second embodiment 100 of the device of the present invention. The device 100 is like device 40 except that instead of using two pairs 70, 72 of telescoping members 74 and 76, only a single pair 104 is used. The single pair 104 is located essentially on the medial plane 80 whereby essentially balanced forces are transmitted to the two molar brackets 60, 62. The use of like reference numerals in FIGS. 1 through 7 is intended to designate like component parts.

Figure 8:
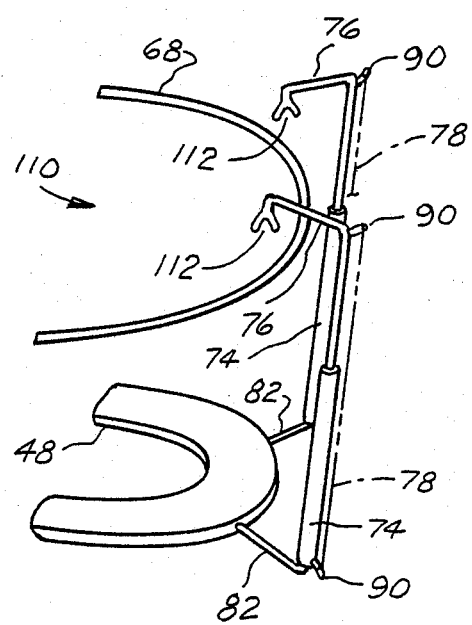
FIG. 8 is a perspective view similar to FIG. 1 illustrating a third embodiment of the device.
Figure 9:
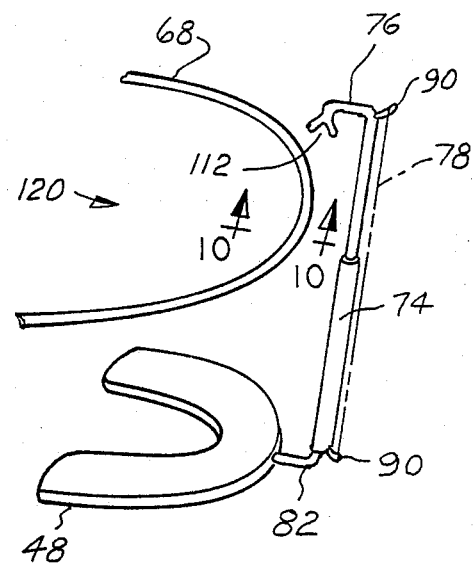
FIG. 9 is a perspective view similar to FIG. 1 illustrating a fourth embodiment of device.
Figure 10:
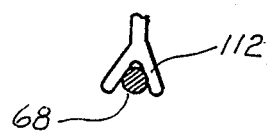
FIG. 10 is a fragmentary sectional view taken in the direction of arrows 10—10 in FIG. 9 but with the parts in different position from that illustrated in FIG. 9.

FIGS. 8 and 9 portray, respectively, a third embodiment 110 and a fourth embodiment 120 which are very similar to embodiments 40 and 100 respectively and therefore like reference numerals are used to designate like parts. The two embodiments 110, 120 differ from embodiments 40, 100 in that the connection of the rods 76 to the wire 68 is a separable one in devices 110, 120. Instead of the free ends of the rods 76 being soldered to the wire 68 as in devices 40, 100, the ends of rods 76 in devices 110, 120 are provided with downwardly facing forks 112. The forks are shaped to fit onto wire 68 in the manner shown in FIG. 10. By virtue of the separable connection, wire 68 can remain intra-orally disposed in the patient while the chin pad and the force-creating means are rendered removable. Such removability may be desirable for certain patients.

Figure 11:
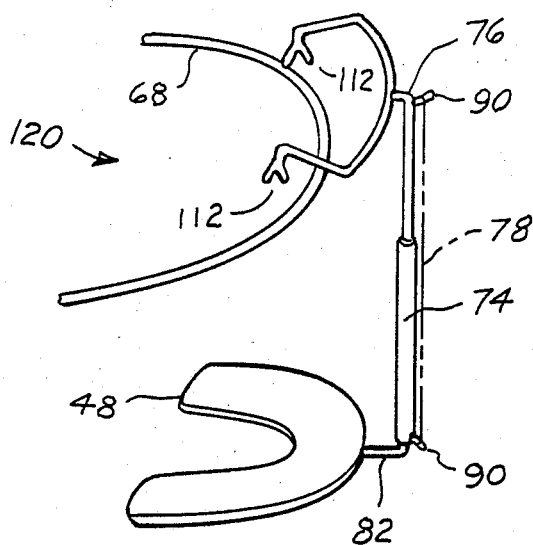
FIG. 11 is a perspective view similar to FIG. 1 illustrating a fifth embodiment of device.

FIG. 11 portrays a still further embodiment 120 of device which incorporates a single force-creating means 104 lying essentially in plane 80 but in which the free end of rod 76 is soldered to a wire bridge 122 which extends to respective sides of plane 80. These respective sides of bridge 122 are shaped to extend inwardly and terminate in downwardly facing forks 112 for separably connecting to wire 68 in the manner portrayed in FIG. 10. Although not shown by separate drawing figures, further embodiments could comprise two force-creating means, as portrayed in FIGS. 1 or 8 for example, having the two rods 76 bridged in the manner of FIG. 11 and terminating in either single or plural forks for separable connection to wire 68.

Figure 12:
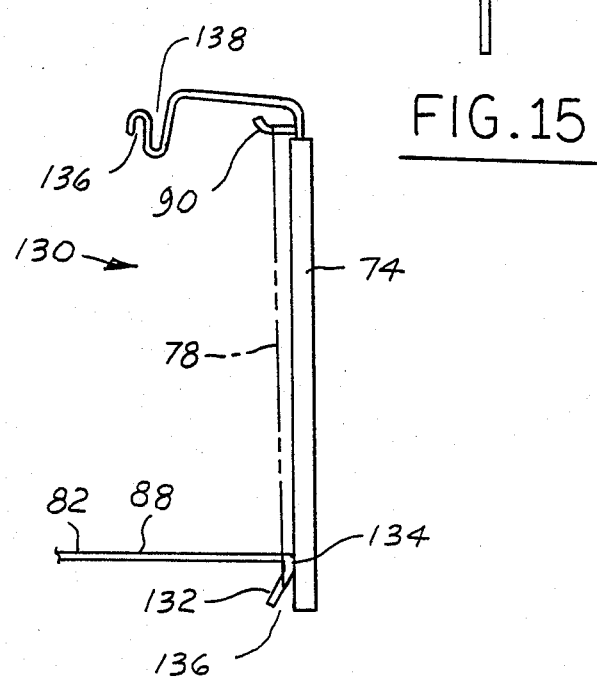
FIG. 12 is a fragmentary side elevational view of a modification to one portion of the device.

FIG. 12 illustrates a modified form of force-creating means 130. The tube 74 and rod 76 are still telescopically engaged; however, the end segment 88 of wire 82 is bent in the manner shown at 132 and soldered at 134 to the outside of tube 74. This leaves a crevice space 136 through which the rubber band 78 can pass. The hook 90 on rod 76 is reversed essentially 180 degrees from the position shown in the preceding embodiments and the opposite end of the rubber band passes around hook 90.

The force-creating means 130 has a separable connection to wire 68. This separable connection is in the form of a hook-like attachment which can be configured, if desired, for a snap fit with wire 68. The free end of rod 76 is shaped to have a double reversal bend consisting of the bends 136, 138 with the bend 138 providing a generally semi-circular throat for separably fitting onto wire 68, either with a snap-fit, or with a close non-snap-fit.

Figure 14:
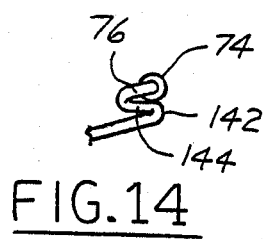
FIG. 14 is a fragmentary view looking in the direction of arrow 14 in FIG. 13.
Figure 13:
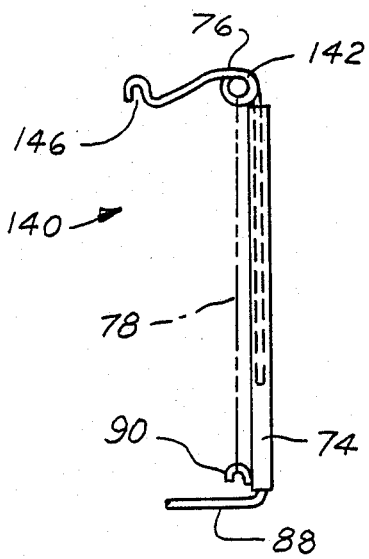
FIG. 13 is a fragmentary side elevational view of another modification.

FIGS. 13 and 14 portray another embodiment of force-creating means 140. The lower hook 90 on tube 74 is reversed approximately 180 degrees from the position shown in device 40, for example. The hook 90 in the rod 76 is replaced by the integral formation of a 360 degree helical loop 142 adjacent where the rod exits the tube. The helical loop has a sufficient clearance 144 allowing the rubber band to be engaged in the manner shown such that the upper end of the rubber band passes through the loop 142. The lower end of the rubber band fits onto hook 90. The force-creating means 140 comprises the free end of rod 76 to have a separable connection with wire 68. This is provided by a single curved bend 146 which provides an open throat for fitting onto wire 68 with either a snap-fit or a non-snap-fit, depending upon the size of the throat.

Figure 16:
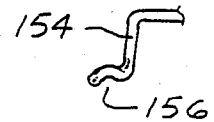
FIG. 16 is a fragmentary view looking in the direction of arrow 16 in FIG. 15.
Figure 15:
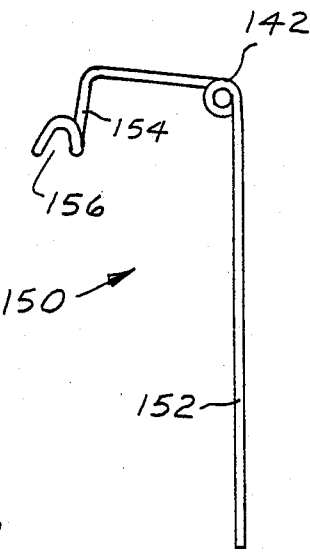
FIG. 15 is a side elevational view illustrating a further modification.

FIGS. 15 and 16 portray yet another embodiment 150 of force-creating means but in the two figures only the rod 76 is shown. The rod comprises a straight portion 152 which telescopes within tube 74, and like embodiment 140, it comprises the helical loop 142 for receiving one end of the rubber band. The free end of rod 76 is shaped with a compound double reversal bend consisting of a first curved bend 154 and a second curved bend 156, the two curved bends being non-coplanar and indeed being in planes at about 90 degrees to each other. The bend 156 provides a throat which fits onto wire 68 in either a snap-fit or non-snap-fit manner, as described earlier.

Figure 17:
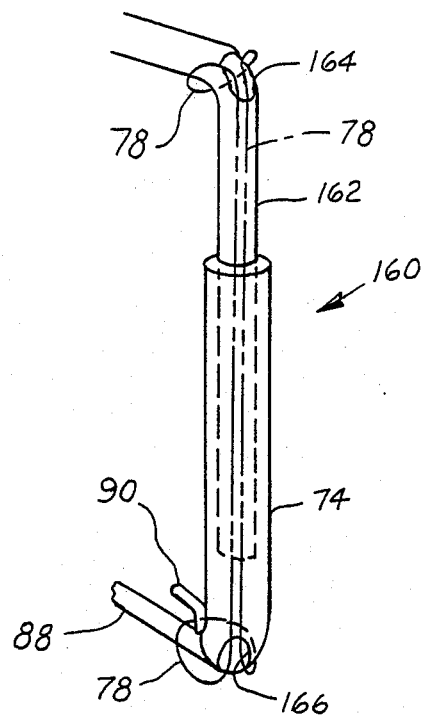
FIG. 17 is a fragmentary perspective view illustrating still another modification.

FIG. 17 illustrates still another embodiment 160 of force-creating means. In this embodiment the rod 76 is replaced by a tube 162 which has a telescopic fit with tube 74. A hole 164 is provided in wall of tube 162, as shown, at the transition from vertical to horizontal. Tube 74 is also provided with a hole 166 at its lower end. The hook 90 is attached on tube 74 to face inwardly toward the chin pad. Essentially the entirety of rubber band 78 is disposed interiorally of the telescopically engaged tubes. At its upper end, the rubber band exits hole 164 to be looped around the bend in tube 162 in the manner shown and at its lower end the rubber band exits hole 166, is conducted to one side, and is looped around hook 90. Essentially entirely concealing the rubber band can offer functional and appearance benefits.

Figure 18:
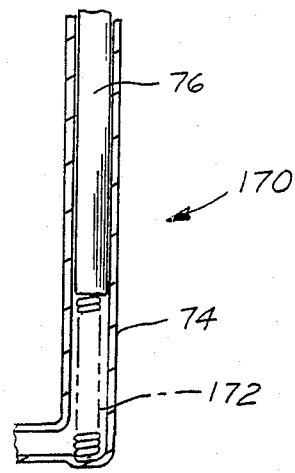
FIG. 18 is a fragmentary side elevational view, partly in section, illustrating yet another modification.
Figure 19:
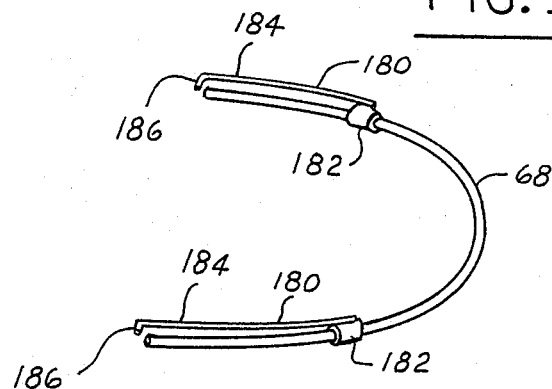
FIG. 19 is a perspective view illustrating a modification to another portion of the device.
Figure 23:
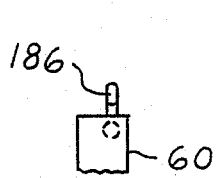
FIG. 23 is a side elevational view of FIG. 21.

The embodiment 170 of FIG. 18 does not utilize a rubber band but rather uses a small helical coil spring 172 disposed within tube 74. The lower end of spring 172 is anchored to the bottom of tube 74; the upper end is anchored to the lower end of rod 76. In response to upward telescoping of the rod with respect to the tube, the spring will be stretched thereby creating a force resisting the motion and urging the rod and tube toward increasing telescopic engagement.

Figure 21:
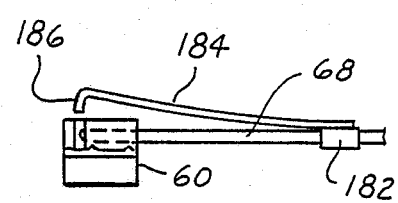
FIGS. 20 and 21 are fragmentary top plan and side elevational views respectively illustrating further details of the modification of FIG. 19.
Figure 22:
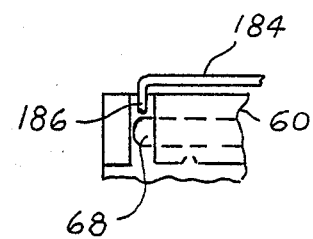
FIG. 22 is an enlarged view of a portion of FIG. 21 showing further detail.
Figure 20:
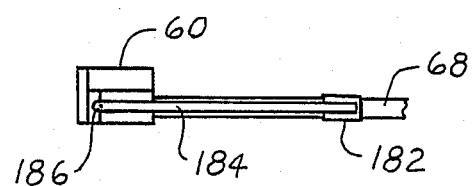

FIGS. 19 through 23 illustrate a modification to wire 68 which is especially advantageous. Briefly, a pair of snap catches 180 are provided adjacent the distal ends of wire 68. The illustrated embodiment of snap catch 180 comprises a short tubular sleeve 182 which is fitted closely onto wire 68 and secured to the wire by any suitable means such as soldering or crimping. The sleeve is spaced mesially of the distal end of the wire. A resilient elongated snap catch element 184 has its mesial end joined to sleeve 182 by any suitable means such as soldering and it extends distally to terminate in a short hook 186 at its distal end adjacent the distal end of wire 68. The construction is such that the hook 186 is disposed slightly beyond the distal end of wire 68 or alternatively such that the end of the hook hits the side of wire 68. In either case, the element 184 can be flexed to a position such as shown in FIGS. 20 and 21 whereby the hook end is spaced from the wire in an amount sufficient to allow the distal end of the wire to pass into and out of the buccal tube on the molar bracket 60. When the element 184 is allowed to relax, the hooked end is urged back toward the wire so that when the wire 68 is disposed within the buccal tube as shown in FIG. 22, the hooked end enters into an interference relationship with the distal end of the buccal tube preventing the corresponding distal end of the wire 68 from being removed from the buccal tube. Hence, the catch provides an especially convenient means for preventing removal of the wire from the buccal tubes. Yet, installation and intended removal can be easily accomplished simply by flexing the snap catch out of the way and either inserting or removing the distal end of the wire into or from the buccal tube. In the embodiment portrayed in FIG. 3, the distal ends of the wire 68 may have to be bent by a tool in order to prevent removal of the wire and therefore the embodiment portrayed in FIGS. 19 through 23 is desirable because bending of the wire 68 is not required, and it is not essential that a tool be used.

Figure 24:
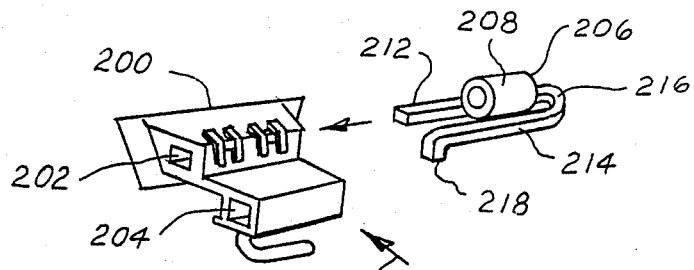
FIG. 24 is an exploded perspective view illustrating another modification.
Figure 25A:
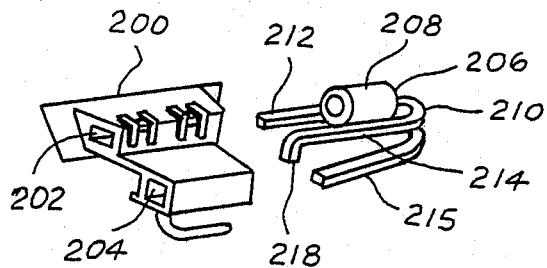
FIG. 25A is an exploded perspective view illustrating a modified form.
Figure 25:
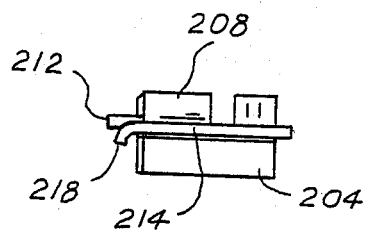
FIG. 25 is a side elevational view looking in the direction of arrow 25 in FIG. 24 illustrating assembled relationship.
Figure 26:
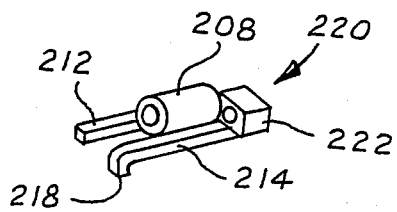
FIG. 26 is a perspective view of a further modification.

FIGS. 24 through 26 illustrate a way of adapting existing components for use with the intrusion device of the present invention. A molar bracket 200 comprises a double buccal tube 202, 204. The illustrated tubes are of non-circular cross section. This component is adapted for reception of a circular wire 68 by use of an adapter 206 which contains a circular buccal tube 208. The tube 208 is attached to a formed wire element 210.

The wire element 210 is formed into a general U-shaped configuration having two parallel sides 212, 214 and a base 216. The free end of side 214 is bent downwardly at 218. The wire 210 has a rectangular cross sectional shape just slightly smaller than that of buccal tube 202. The side 212 of wire 210 can be inserted mesially into tube 202 entering the distal end of the tube 202 in the manner shown in FIG. 24. The downwardly turned end 218 of side 212 is flexed slightly from its free position and passes over the top of buccal tube 204 during this process.

In the fully assembled position portrayed in FIG. 25, end 218 has cleared buccal tube 204 and the wire relaxes to assume the shape shown in that Figure. Any substantial mesial displacement of the adapter from its assembled position is prevented by abutment of the base 216 of the U with the distal end of buccal tube 202. Any substantial distal movement is prevented by the downwardly turned end 218 hitting the mesial end of buccal tube 204. In the assembled position the tube 208 is supported on the double buccal tube overlying tube 204 and being labial of tube 202. While this assembly will provide substantial stability, it is always possible to ligate the adapter to the double buccal tube if desired.

A modified form of adapter 206 is shown in FIG. 25A to comprise for wire 210 a further side 215 which is inserted into tube 204. This additional side 215 is joined to the wire 210 in any conventional manner and is for the purpose of providing additional stability for supporting the tube 208 on bracket 200.

FIG. 26 shows a modified form of adapter 220 which is like adapter 206 but with the inclusion of a further tube 222 supported distally and labially of the circular tube 208. In use, the wire 68 is disposed within tube 208 and can be secured in any of the manners described earlier. The further tube 222 is available for use with a further wire (not shown).

The use of the adapters as portrayed in FIGS. 24–26 is advantageous because it allows a patient who may already have brackets 200 to receive the intrusion device of the present invention without having to have those brackets replaced. Of course, the configurations portrayed in FIGS. 24 through 26 could be applied at the beginning of initial treatment.

Figure 27:
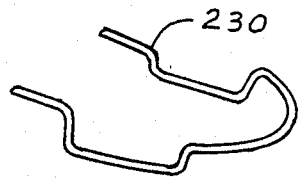
FIG. 27 is a perspective view of a still further modification.

FIG. 27 portrays the use of a utility arch wire 230 in place of the fine arch wire shown in the preceding figures. The particular choice of the intra-oral means 44 will depend on the nature of the individual patient's condition and therefore it is, as explained above, to be appreciated that the illustrated examples are merely representative.

Figure 28:
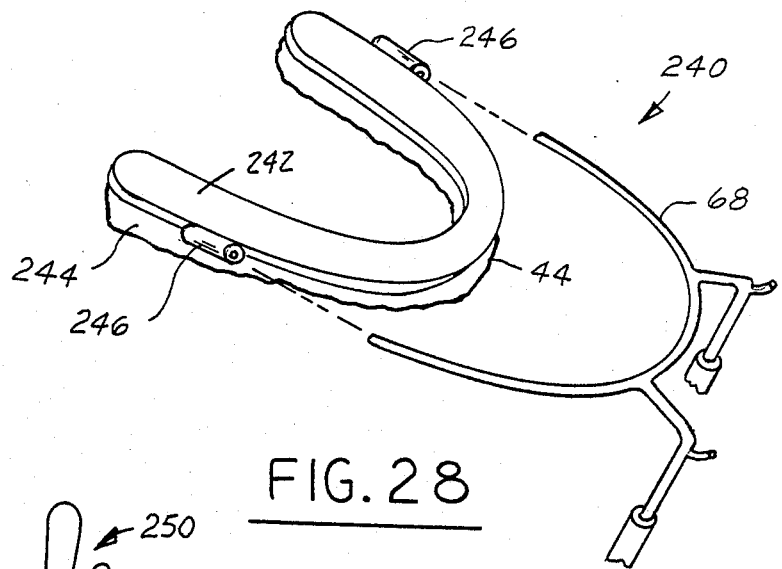
FIG. 28 is an exploded perspective view of a portion of another embodiment of device.

FIG. 28 illustrates a further embodiment 240 in which the intra-oral means 44 comprises a rigid splint 242 which is fitted onto the arch via tooth positioner or gummy retainer material 244. Tubes 246 are provided as shown for reception of the wire 68, and when desired the tubes may be crimped onto the wire.

Figure 29:
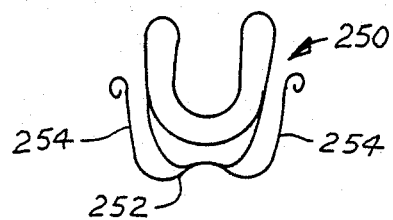
FIG. 29 is a top plan view of still another embodiment of device.
Figure 30:
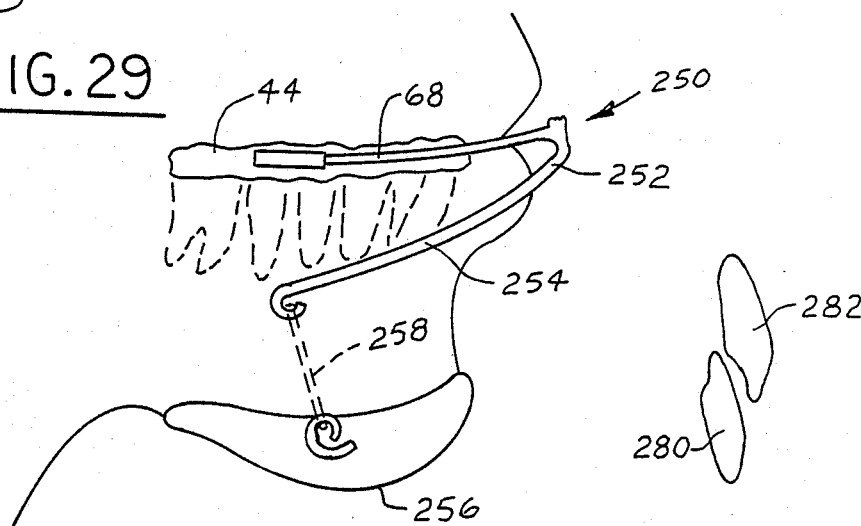
FIG. 30 is a side elevational view of the device of FIG. 29 on a larger scale and illustrating usage in a patient.

FIGS. 29 and 30 illustrate still another embodiment 250 in which the force-creating means and the extra-oral means 48 are somewhat different from preceding embodiments. In FIGS. 29 and 30 a face bow 252 is used to make connection to the intra-oral means 44. The two arms 254 of the face bow attach to a conventional chin cup 256 by means of rubber bands 258 in the manner shown.

Figure 31:
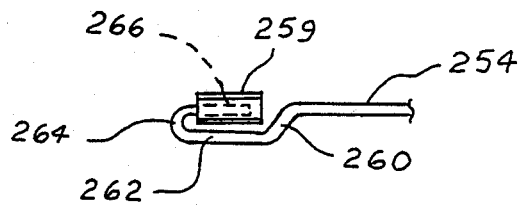
FIG. 31 is a fragmentary side elevational view of a modification.

FIG. 31 illustrates a modification to the face bow. Rather than the free ends of the face bow's arms 254 being essentially straight for insertion into the mesial ends of the tubes 259 on the intra-oral means 44, the free ends of the face bow's arms are configured for distal insertion. As such each free end comprises an offset bend 260 which leads to a relatively straight segment paralleling the corresponding tube 259. A reverse bend 264 at the distal end of segment 262 leads to a mesially extending, relatively straight segment 266 which is inserted into the distal end of the tube. The relative dimensions of the several portions 260, 262, 264, and 266 are such that the segments 266 can be inserted into and removed from the distal ends of the tubes 259 without interference. The abutment of the reverse bends 264 with the distal ends of the tubes positively establishes the mesial limit of the face bow, and hence can offer certain advantages over the conventional means of attachment depicted by FIGS. 28–30.

Figure 32:
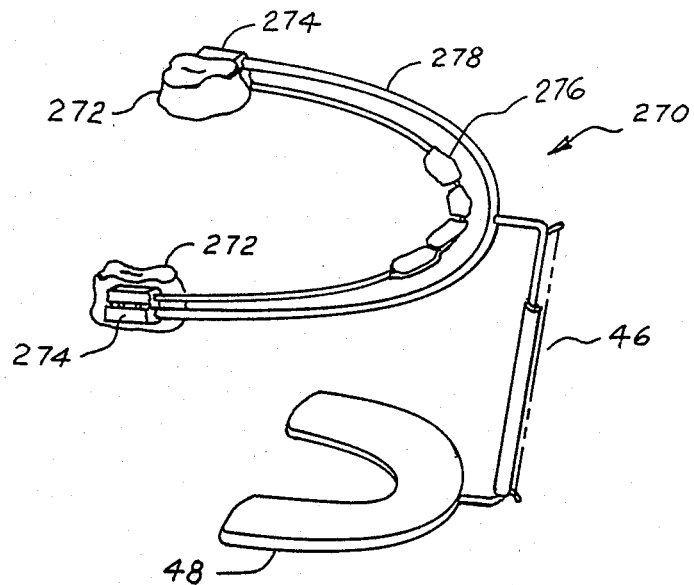
FIG. 32 is a perspective view of yet another embodiment of device.

FIG. 32 shows a still further embodiment 270 of the invention which is intended to eliminate the use of bonding. Rigid plastic caps 272 each containing at least a double buccal tube 274, or equivalent, are fitted onto molar teeth. A Crozat extension 276 is inserted into the tubes and fitted to the incisors. A wire 278 is also fitted to the tubes and is cooperatively associated with a chin pad 48 by any suitable one of the previously described force-creating means 46. The means 46, acts through wire 278 and the buccal tubes 274 to cause an intrusion force to be developed by the Crozat extension thereby producing the desired tooth intrusion.

Figure 33:
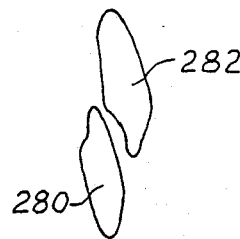
FIGS. 33 and 34 are respective elevational views of teeth in upper and lower arches for purposes of explaining treatment performed by the device of the present invention.
Figure 34:
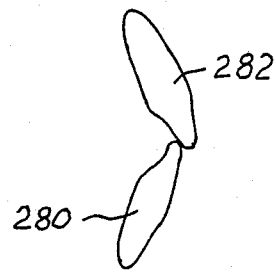

FIG. 33 illustrates an orthodontic correction in which intrusion of a lower arch tooth 280 is desirable. The condition of FIG. 33 illustrates an overbite wherein the upper and lower arch teeth 282, 280 have too much overlap. By use of the intrusion device of the invention, the lower arch tooth may be intruded to a corrected condition such as shown in FIG. 34.

The foregoing embodiments of the invention provide the attending professional orthodontist with a high degree of versatility in treating particular conditions of individual patients. As in any orthodontic treatment procedure, the skill of the professional is invaluable in achieving best results. Therefore, it is to be appreciated that the disclosed embodiments of appliance are intended to be representative of generic principles. Certain features have utility by themselves and therefore are useful not only in this dental intrusion appliance but in other devices as well. The nature of correction to be performed for any individual will depend upon the individual's particular condition and therefore the selection of any particular form of the device for any particular individual will be made by the treating professional. For some individuals undergoing treatment, the professional may deem that the appliance should be non-removable so that the individual cannot interrupt the procedure. For others, a removable appliance may be suitable, and therefore removable embodiments will be advantageous in such circumstances. Over the course of treatment procedure, it is entirely possible that different forms of appliances may be used, and/or any given appliance modified, based upon course of treatment. While certain detailed embodiments of the invention have been disclosed, the manner of fabrication is performed using conventional fabrication procedures, such as joining, wire bending, crimping, etc.

While a preferred embodiment of the invention has been disclosed, it will be appreciated that principles are applicable to other embodiments.

I claim:

1. A dental intrusion device for performing intrusion of one or more teeth of a dental arch into the gingiva comprising intra-oral means for mesio-distally spanning at least a portion of the dental arch and for joining certain of the teeth so spanned including at least those teeth which are to be intruded, force-creating means extending from said intra-oral means to an extra-oral means and acting in the same sense as the direction of intrusion, the force developed by said force-creating means being reacted by said extra-oral means and said intra-oral means in a manner causing intrusion forces to be developed on those teeth of the arch which are to be intruded, in which said intra-oral means is adapted for acting on teeth of the lower arch, and said extra-oral means comprises chin-engaging means, said force-creating means extending between said chin-engaging means and said intra-oral means.

2. A device as set forth in claim 1 in which said chin-engaging means comprises a chin cup, and said force-creating means comprises a face bow which extends into intra-oral connection with said intra-oral means and which has external limbs, and means connecting the external limbs of the face bow with the chin cup.

3. A device as set forth in claim 1 in which said force-creating means comprises telescopically engaged members and resilient means urging the telescopically engaged members in a sense of increasing telescopic engagement.

4. A device as set forth in claim 3 in which said resilient means comprises a rubber band which is in tension between the telescopically engaged members urging them toward increasing telescopic engagement.

5. A device as set forth in claim 4 in which said members comprise telescopically engaged tubes with openings at selected portions of their respective walls, said rubber band having a medial portion disposed within the telescopically engaged tubes and end portions exiting the respective tubes via their respective openings and means for anchoring respective end portions of the rubber bands on respective ones of the telescopically engaged tubes.

6. A device as set forth in claim 4 including hooks on the exterior of the telescopically engaged members and in which said resilient means comprises an endless rubber band passing around the hooks.

7. A device as set forth in claim 6 in which one of said hooks is formed in a wire which extends from a corresponding one of said telescopically engaged members to said chin-engaging means.

8. A device as set forth in claim 3 in which said resilient means comprises a helical coil spring disposed internally of one of said members and having respective points of anchoring on said one member and on the other of said members respectively.

9. A device as set forth in claim 3 in which one of said telescopically engaged members comprises an integral loop exterior of that member's telescopic engagement with the other member, said integral loop providing a point of anchoring for said resilient means.

10. A device as set forth in claim 3 in which the connection of said force-creating means to said intra-oral means comprises a separable connection between one of said telescopically engaged members and said intra-oral means.

11. A device as set forth in claim 10 in which the separable connection is provided by a downwardly facing fork on said one member, said intra-oral means comprising a wire which is separably engaged by said fork.

12. A device as set forth in claim 10 in which the separable connection of said one member to said intra-oral means comprises a bend formed in an end portion of said one member to have a downwardly open throat.

13. A device as set forth in claim 3 in which said force-creating means is disposed in a medial plane through the arch.

14. A device as set forth in claim 13 including means extending from one of said members to respective sides of the medial plane for connection with said intra-oral means at locations disposed on opposite sides of the medial plane.

15. A device as set forth in claim 3 comprising two such pairs of telescopically engaged members, each pair being disposed to a corresponding side of a medial plane through the arch.

16. A device as set forth in claim 15 in which said two pairs of telescopically engaged members each has its own separable connection with said intra-oral means.

17. A device as set forth in claim 1 in which said chin-engaging means comprises a pad having a body and a wire having a medial portion embedded within said body, said wire having an external portion which projects anteriorly of the body and supports said force-creating means.

18. A device as set forth in claim 17 in which said wire comprises two external portions which project from said body at locations disposed on respective opposite sides of a medial plane through the arch.

19. A device as set forth in claim 1 in which said intra-oral means comprises a wire spanning the arch and connected to molar brackets on opposite sides of the arch.

20. A device as set forth in claim 19 including hooks on said wire disposed mesial of the molar brackets, said hooks hooking onto said wire in mesially spaced relation to the point of connection of the wire to the brackets.

21. A device as set forth in claim 19 in which said intra-oral means comprises a fine arch wire which attaches to selected teeth of the arch via brackets.

22. A device as set forth in claim 19 in which said intra-oral means comprises a splint which fits onto the arch through tooth positioner material and tubes into which the distal end portions of the wire are inserted.

23. A device as set forth in claim 19 in which said wire includes snap catches at its distal end portions for releasably connecting the distal end portions with buccal tubes on the molar brackets.

24. A device as set forth in claim 23 in which said snap catches comprise sleeves fitting onto the wire and elongate resilient elements extending distally from the respective sleeves and terminating in hooked ends for hooking behind the buccal tubes on the molar brackets.

25. A device as set forth in claim 19 in which said wire connects to a molar bracket via an adapter tube which is separably attached to buccal tubes on the molar bracket.

26. A device as set forth in claim 25 in which said adapter tube is separably attached to the buccal tubes on the molar bracket by its own U-shaped wire.

27. A device as set forth in claim 26 including a further tube disposed on said U-shaped wire.

28. A device as set forth in claim 1 in which a face bow extends from said intra-oral means to said force-creating means, and said face bow has the free ends of its limbs configured so as to be distally inserted into buccal tubes on said intra-oral means.

29. A device as set forth in claim 1 in which said intra-oral means comprises caps for fitting onto molar teeth, a Crozat extension from said caps for fitting onto incisors, and a wire extending from said caps, said force-creating means acting on said wire for causing tooth intrusion forces to be developed in said Crozat extension.

30. Means for adapting a molar bracket having a pair of buccal tubes comprising an adapter element in the form of a U-shaped wire having a base and a pair of sides extending from the base, one of said sides fitting into one of the two buccal tubes of the molar bracket and the other of said sides being disposed in supported relationship on the other tube of the molar bracket, a further tube supported on the U-shaped wire externally of said buccal tubes and said other side including at its free end a bend which, when the adapter is assembled to the buccal tubes, is disposed mesially beyond the mesial end of the other buccal tube so as to be in an interference relationship with attempted distal displacement of the adapter.

31. Means as set forth in claim 30 including a second tube disposed on said U-shaped wire.

32. Means as set forth in claim 30 including on said wire a further side which fits into said other buccal tube.

33. In an orthodontic appliance having a face bow whose limbs are inserted into buccal tubes, the improvement which comprises the free end of at least one of the face bow's limbs comprising a segment which parallels and is exterior to the corresponding tube, a reverse bend at the distal end of said segment, and a mesially extending segment extending from said reverse bend removably engaged in the distal end of the corresponding tube.

* * * * *